United States Patent [19]

White

[11] Patent Number: 4,661,625
[45] Date of Patent: Apr. 28, 1987

[54] SYNTHESIS AND PURIFICATION OF D-PROPOXYPHENE HYDROCHLORIDE

[75] Inventor: Carl R. White, St. Louis, Mo.

[73] Assignee: Mallinckkodt, Inc., St. Louis, Mo.

[21] Appl. No.: 803,321

[22] Filed: Dec. 2, 1985

[51] Int. Cl.$^4$ .............................................. C07C 67/00
[52] U.S. Cl. ...................................................... 250/560
[58] Field of Search ............................... 560/250, 253

[56] References Cited

FOREIGN PATENT DOCUMENTS 1568252  1/1973  Fed. Rep. of Germany ...... 560/250
1793640  4/1973  Fed. Rep. of Germany ...... 560/250

OTHER PUBLICATIONS

Pohland et al., "J. Amer. Chem. Soc." vol. 75, (1953), pp. 4458–4461.
Pohland et al., "J. Amer. Chem. Soc." vol. 77, (1953), pp. 3400–3401.
Pohland, et al., "J. Organic Chem." vol. 28, (1963), pp. 2483–2484.
Noller, "Chemistry of Organic Compounds" (1965), pub. W. R. Saunders Co. Phila., p. 711.

Primary Examiner—Werren B. Lone
Attorney, Agent, or Firm—Veo Peoples, Jr.

[57] ABSTRACT

New and improved synthesis of α-d-propoxyphene hydrochloride by acid chloride reaction between propionyl chloride and α-d-1,2-diphenyl-3-methyl-4-dimethylamino-2-butanol (d-oxyphene) with small amounts of thionyl chloride improves yield and substantially simplifies purification.

18 Claims, No Drawings

SYNTHESIS AND PURIFICATION OF D-PROPOXYPHENE HYDROCHLORIDE

BACKGROUND OF THE INVENTION

Of the many phenylpropylamines which show analgesic activity, the two most important are methadone and propoxyphene. The optically active alpha-dextro stereoisomer of propoxyphene is the only stereoisomer of propoxyphene which possesses analgesic properties. It is commonly prescribed in its hydrochloride salt form which is a bitter, white crystalline powder freely soluble in water and soluble in alcohol. Its chemical name is α-d-1,2diphenyl-2-propionoxy-3-methyl-4-dimethylamino butane hydrochloride and is sold under several different trademarks including for example DARVON, DOLENE, and SK-65. α-d-Propoxyphene is probably comparable to codeine as an analgesic and is widely prescribed in combination with aspirin for the treatment of mild to moderate pain that is not adequately relieved by aspirin alone. Combinations of d-propoxyphene and aspirin (like those of codeine and aspirin) are more effective than either agent alone.

Preparation of d-propoxyphene was first described by A. Pohland and H. R. Sullivan at *J. Am. Chem. Soc.*, Volume 75, pp. 4458(1953). Therein, the authors disclosed a synthesis involving several stages, (1) preparation of an aminoketone called β-dimethylaminobutrophenone by addition of the secondary amine to phenylpropenyl ketone; (2) a Grignard reaction of the amino ketone with benzylmagnesium chloride to yield the amino, hydrochloride-carbinols described as α-(75%) and β-(15%) 4-Dimethylamino-1,2-diphenyl-3-methyl-2-butanol Hydrochloride; and (3) acylation of the α-amino carbinol hydrochloride by addition of an equal weight of propionic anhydride and five times that weight of pyridine and heating to reflux for several hours. Note the following reaction formula:

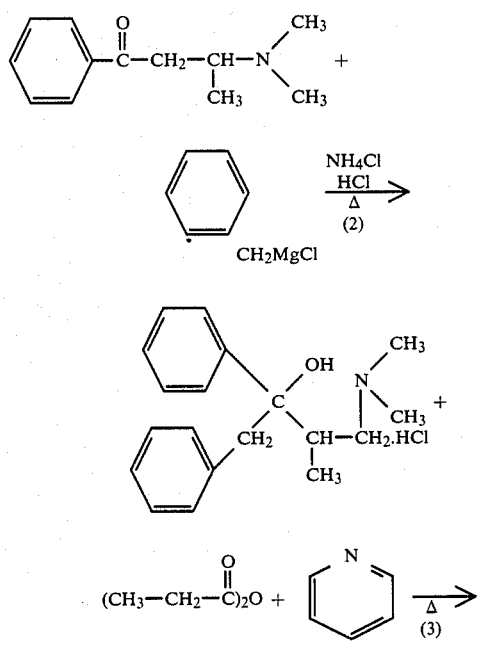

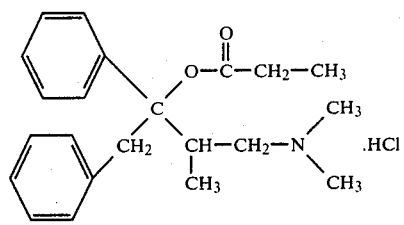

After cooling to recover the crude product, it was purified by two recrystallizations from methanol-ethyl acetate solution resulting in a yield of 70%.

Although this work confirmed that the α and not the β-diastereoisomers of propoxyphene gave rise to analgesic activity, it was still necessary to determine which of the optical forms of the α-diastereoisomer, i.e.- α-d(+) or α-l(−) was responsible for the analgesic activity. Accordingly, Pohland and Sullivan reported in the J. Am. Chem. Soc., Volume 77, pp. 3400 (1955) their work on resolution of α-dl-4-Dimethylamino-1,2-diphenyl-3-methyl-2-butanol by fractional crystallization of its d-camphorsulfonic acid salt. From the respective α-d and α-l carbinol d-camphorsulfonic salts the optically active hydrochloride salts were prepared. The α-d-hydrochloride was acylated using propionic anhydride and triethylamine, while the α-l hydrochloride was acylated using propionic anhydride and pyridine. It was therein found that only the α-d stereoisomer gave the analgesic response. However, final purification of the hydrochloride salt required additional HCl and three recrystallizations and yields of less than about 70%.

In 1963, Pohland, Peters and Sullivan reported in the J. Org. Chem., Vol. 28, pp. 2483, an alternative synthetic route for α-d-propoxyphene hydrochloride. Working backwards from the desired optically active isomer of propoxyphene by its hydrolysis and dehydration to stilbene, followed by ozonization of the stilbene, the authors discovered good yield of (−)-β-dimethylamino-α-methylpropiophenone. This optically active amino ketone was found to be surprisingly stable in salt from thus permitting its use as a starting material for a stereo selective synthesis of α-d-propoxyphene. Racemic β-Dimethylamino-α-methylpropiophenone was resolved by crystallization of the dibenzoyl tartrate salts from acetone solution. The use of dibenzoyl-(−)-tartaric acid yielded the insoluble salt having (−)-β-dimethylamino-α-methylpropiophenone, while the use of the (+) tartaric acid yielded the salt having the (+)-amino ketone isomer.

It is of interest that according to this reported synthesis, it was the (−) isomer of β-dimethylamino-α-methylpropiophenone, which when liberatd from its (−) tartrate salt by Grignard reaction with benzylmagnesium chloride provided good yields of the (+) or (d) isomer of α-1,2-diphenyl-3-methyl-4-dimethylamino-2-butanol which of course is the carbinol precursor for α-d-propoxyphene. The reported yields were 69%. The acylation was accomplished as had been previously reported, i.e., by means of propionic anhydride in either triethylamine or pyridine.

More recently, in May of 1978, Hungarian Pat. No. 14,441 issued disclosing a synthesis of α-d-propoxyphene employing the above-described method except that (1) the (+)tartaric acid was employed in the resolution of the racemic β-dimethylamino-α-methylpropiophenone and (2) the acylation was accomplished by reacting triethylamine in chloroform, propionyl chloride and the carbinol rather than propionyl anhydride and the carbinol hydrochloride. Still the product was precipitated in ether and required an amine catalyst.

Nevertheless, the reported yields of α-d-propoxyphene by the prior art anhydride esterifications are improved upon by the present invention.

SUMMARY OF THE INVENTION

The new and novel process of the present invention involves an acid chloride reaction rather than an anhydride esterification. Acylating the α-d carbinol precursors into α-d propoxyphene by adding propionyl chloride and thionyl chloride in dichloromethane forms the process of the invention.

It is the object of the present invention to provide a more effective method of preparing α-d propoxyphene. It is a further object of this invention to provide a more effective purification of α-d propoxyphene.

DETAILED DESCRIPTION AND PREFERRED EMBODIMENTS

In the process of this invention α-d propoxyphene hydrochloride is prepared by acid chloride conversion of the carbinol known as α-1,2-diphenyl-3-methyl-4-dimethylamino-2-butanol (hereinafter referred to as d-oxyphene). This precursor carbinol, d-oxyphene is well-known in the art and can be derived from any of several prior art methods, including those hereinbefore described.

The d-oxyphene is reacted with propionyl chloride in a solvent, preferably dichloromethane. It has been discovered that a relatively small proportion of thionyl chloride, when added thereto, enables more complete separation of the final α-d propoxyphene from unreacted d-oxyphene, by conversion of the unreacted carbinol, d-oxyphene, to its corresponding alkyl halide. Subsequently, the dichloromethane is evaporated and the residue treated with ethyl acetate to dissolve the organic by-products. The purified α-d propoxyphene hychloride is recovered at yields in excess of 70%. Unlike the prior art methods which required precipitating the final product in ether and multiple recrystallizations from methanol-ethyl acetate, the purification step of the present invention permits recovery of pure product by merely filtering it out of the ethyl acetate solution. By introducing thionyl chloride which selectively reacts with the carbinol, d-oxyphene, its separation from the final product may be greatly facilitated while simultaneously enhancing its conversion to α-d-propoxyphene hydrochloride.

The reaction is conducted in a solvent, preferably dichloromethane, present in amounts sufficient to completely dissolve the reaction mixture. In one preferred embodiment of this invention, the use of 5.0 milliliters of dichloromethane per gram of d-oxyphene will completely sustain the reaction. Larger volumes of the solvent may be employed if desired. Other solvents suitable for use in the reaction mixture must be able to keep all the reactants in solution throughout the reaction without interfering with its completion. Included among such solvents are other chlorinated compounds such as chloroform.

The reaction of this invention may be conducted by adding propionyl chloride to d-oxyphene in the range of from about 1:1 to about 10:1 moles of the acid chloride per mole of d-oxyphene, preferably 1:1 to 4:1. It is especially preferred to use about 2 moles of propionyl chloride per mole of d-oxyphene.

To the reaction mixture is added thionyl chloride in an amount ranging from about 0.01 moles to 0.50 moles per mole of d-oxyphene, preferably from 0.01:1 to about 0.20:1. It is especially preferred to add about 0.15 moles of the thionyl chloride per mole of d-oxyphene.

The reaction proceeds spontaneously although it is preferred to conduct the reaction at such a rate that the temperature does not exceed 30°–40° C. It is in particularly preferred to maintain the reaction temperature at between 20° an 25° C. The solvent is evaporated from the mixture after the reaction is complete, followed by sufficient addition of a solvent preferably ethyl acetate to selectively dissolve substantially all of the organic by-products and permit the α-d-propoxyphene hydrochloride to be filtered off.

The following example is offered by way of illustration and not by way of limitation.

EXAMPLE I

To 500 ml. of dichloromethane in a 1000 ml. round bottom flask under nitrogen purge, was added 100.0 gm. (353 mmols) of d-oxyphene. While cooling the flask in an ice water bath, 65.4 gm. (700+ mmols) of propionyl chloride were added at a rate sufficient to maintain the temperature of the reaction mixture at between about 20° and 25° C. The ice bath was removed and the mixture stirred for one hour. Then added to the mixture while still stirring, 6.1 gm. (51 mmols) of thionyl chloride. The mixture continued to be stirred for one hour. Then the solvent and other volatiles were vacuum distilled, leaving a heavy, amber-colored oil. To it were added 287 ml. of ethyl acetate and the mixture was stirred for two hours resulting in a fine white precipitate. These white solid particles were collected under vacuum on a Buchner funnel and washed thoroughly with ethyl acetate. Upon drying at 80° C., a yield of 100.7 gm. (76%) α-d propoxyphene was recovered having analytical purity.

What is claimed is:

1. In a method for making alpha-d-propoxyphene comprising reacting d-oxyphene and propionyl chloride in a chlorinated solvent, the improvement comprising adding thionyl chloride to the reaction mixture in an amount of at least about 0.01 moles per mole of d-oxyphene, evaporating the solvent, treating the residue with ethyl acetate, and recovering the alpha-d-propoxyphene by filtration;

whereby the need for precipitation of the product in ether and multiple crystallization is substantially negated.

2. The method of claim 1 wherein the amount of thionyl chloride added relative to the amount of d-oxyphene is a mole to mole ratio of from about 0.1:1.0 to about 0.5:1.0.

3. The method of claim 2 wherein the ratio ranges from about 0.1:1.0 to about 0.2:1.0.

4. The method of claim 2 wherein the ratio is 0.15:1.0.

5. The method of claim 1 wherein the reactants are in a dichloromethane solution.

6. The method of claim 5 wherein the dichloromethane is present in a volume at ambient conditions about 5.0 ml. per gram of d-oxyphene.

7. The method of claim 1 wherein the ratio of propionyl chloride to d-oxyphene ranges from about 1.0:1.0 to about 10.0:1.0 by gm. moles.

8. The method of claim 7 wherein the ratio ranges from 1.0:1.0 to about 4.0:1.0.

9. The method of claim 7 wherein the ratio is 2.0:1.0.

10. A method for making α-d propoxyphene hydrochloride comprising reacting propionyl chloride and d-oxyphene at a relative gram mole ratio of from about 1:1 to about 10:1 in dichloromethane solution to dissolve the reactants, admixing an amount of thionyl chloride of at least about 0.1 moles per mole of d-oxyphene sufficient to selectively react with the unreacted d-oxyphene, separating the solvent selectively dissolving the organic by-products, and purifying the α-d propoxyphene by filtration;

whereby the need for precipitating the α-d-propoxyphene in ether, and fractionally crystallizing it in methanol-ethyl acetate is substantially negated, while the yield is substantially improved.

11. The method of claim 10 wherein the dichloromethane is present in an amount under ambient conditions of about 5 ml. per gram of d-oxyphene.

12. The method of claim 10 wherein the mole ratio of propionyl chloride to d-oxyphene is from about 1:1 to about 4:1.

13. The method of claim 10 wherein the mole ratio is 2:1.

14. The method of claim 10 wherein the mole ratio of thionyl chloride to propionyl chloride is from about 0.01:1.0 to about 0.5:1.0.

15. The method of claim 15 wherein the ratio is from 0.01:1 to 0.20:1.

16. The method of claim 16 wherein the ratio is 0.15:1.

17. The method of claim 1 wherein he reaction is conducted under a nitrogen purge.

18. The method of claim 10 wherein the reaction is conducted under nitrogen purge.

* * * * *